(12) United States Patent
Klawitter et al.

(10) Patent No.: US 8,366,780 B2
(45) Date of Patent: Feb. 5, 2013

(54) SHOULDER JOINT IMPLANT

(75) Inventors: Jerome J. Klawitter, Austin, TX (US); Monti R. Gourley, Austin, TX (US)

(73) Assignee: Ascension Orthopedics, Inc., Austin, TX (US)

( * ) Notice: Subject to any disclaimer, the term of this patent is extended or adjusted under 35 U.S.C. 154(b) by 341 days.

(21) Appl. No.: 12/516,764

(22) PCT Filed: Nov. 28, 2007

(86) PCT No.: PCT/US2007/085791
§ 371 (c)(1),
(2), (4) Date: May 28, 2009

(87) PCT Pub. No.: WO2008/067400
PCT Pub. Date: Jun. 5, 2008

(65) Prior Publication Data
US 2010/0063593 A1 Mar. 11, 2010

Related U.S. Application Data

(60) Provisional application No. 60/867,741, filed on Nov. 29, 2006.

(51) Int. Cl.
*A61F 2/40* (2006.01)
(52) U.S. Cl. .................. 623/18.11; 623/19.11
(58) Field of Classification Search .... 623/19.11–19.14, 623/20.35, 22.17–22.2, 22.24, 22.28–22.29, 623/22.42, 23.11–23.14, 23.42
See application file for complete search history.

(56) References Cited

U.S. PATENT DOCUMENTS

| | | |
|---|---|---|
| 3,707,006 A | 12/1972 | Bokros et al. |
| 4,126,924 A | 11/1978 | Akins et al. |
| 4,166,292 A * | 9/1979 | Bokros ............... 623/21.18 |
| 4,224,699 A | 9/1980 | Weber |
| 4,227,265 A | 10/1980 | Frey |
| 4,241,463 A | 12/1980 | Khovaylo |
| 4,770,658 A | 9/1988 | Geremakis |
| 4,908,034 A * | 3/1990 | Weightman et al. ....... 623/22.43 |
| 4,936,855 A * | 6/1990 | Sherman ............... 623/22.2 |
| 5,062,853 A | 11/1991 | Forte |
| 5,507,826 A | 4/1996 | Besselink et al. |

(Continued)

FOREIGN PATENT DOCUMENTS

| | | |
|---|---|---|
| EP | 1 632 200 | 8/2005 |
| JP | 62-254748 A | 11/1987 |

(Continued)

OTHER PUBLICATIONS

European Patent Office, "Extended European Search Report" dated Nov. 20, 2009 issued in connection with corresponding European Patent Application No. 07871626.3, 5 pages.

(Continued)

*Primary Examiner* — Thomas J Sweet
*Assistant Examiner* — Cheryl Miller
(74) *Attorney, Agent, or Firm* — Fitch, Even, Tabin & Flannery, LLP

(57) ABSTRACT

A prosthetic implant comprising a head having a spherical pyrocarbon shell (13,73) that is attached to a metal substructure (17,77) via an intermediate element (15,45,75). A subassembly of the intermediate element and the pyrocarbon shell may be connected to the metal substructure via a metal split ring (19) that resides partially in each of two facing grooves (33,35) or via interengaging elements (85,87,91) that are provided in two juxtaposed cylindrical surfaces. The design is such that compressive forces applied to the implant at its spherical articulating surface are transferred via compression through the pyrocarbon shell to the metal substructure.

18 Claims, 13 Drawing Sheets

U.S. PATENT DOCUMENTS

| | | | |
|---|---|---|---|
| 5,534,033 A * | 7/1996 | Simpson | 623/13.14 |
| 5,593,445 A | 1/1997 | Waits | |
| 5,755,807 A | 5/1998 | Anstaett et al. | |
| 2003/0187512 A1 | 10/2003 | Frederick et al. | |
| 2004/0122524 A1 | 6/2004 | Hunter et al. | |
| 2005/0220531 A1 | 10/2005 | Sellers et al. | |
| 2007/0225822 A1 * | 9/2007 | Santilli et al. | 623/23.14 |
| 2009/0143865 A1 * | 6/2009 | Hassler et al. | 623/19.11 |
| 2009/0240336 A1 * | 9/2009 | Vander Meulen et al. | 623/18.11 |

FOREIGN PATENT DOCUMENTS

| | | |
|---|---|---|
| JP | 2006-511272 A | 4/2006 |
| WO | WO 2004/026170 | 4/2004 |
| WO | WO 2007/109752 | 9/2007 |

OTHER PUBLICATIONS

Vander Meulen et al, Prosthetic Implant and Assembly Method, U.S. Appl. No. 12/233,976, filed Apr. 23, 2009.

JPO; English translation of Official Notice of Rejection issued in Japanese Patent Application No. 2009-539462; Mailed Sep. 14, 2012; 4 pages.

* cited by examiner

Humeral Head Resurfacing

Humeral Head Replacement

PRIOR ART

FIGURE 2. Shoulder Joint Anatomy

FIGURE 3A
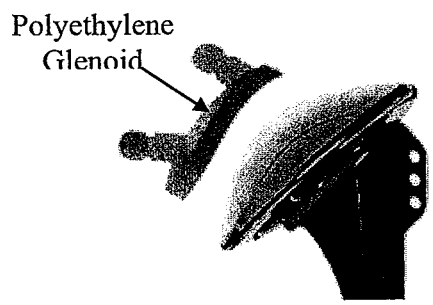
Polyethylene Glenoid
FIGURE 3B
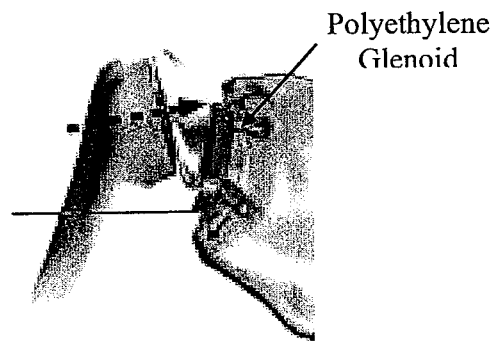
Polyethylene Glenoid
PRIOR ART
FIGURE 4 Spherical Cap Dimensions
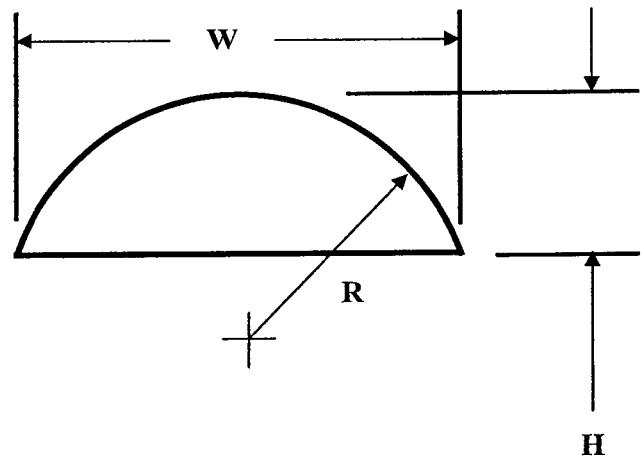
$R = (W^2 + 4H^2) / 8H$
FIGURE 5
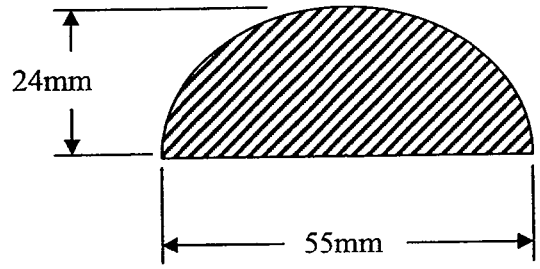
FIGURE 6
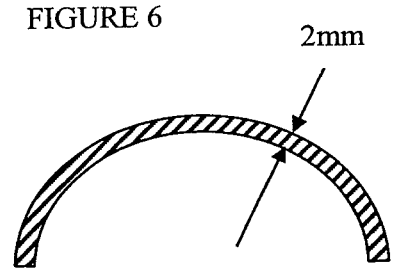
2mm FIGURE 7. Humeral Head Assembly Using Polyethylene Liner
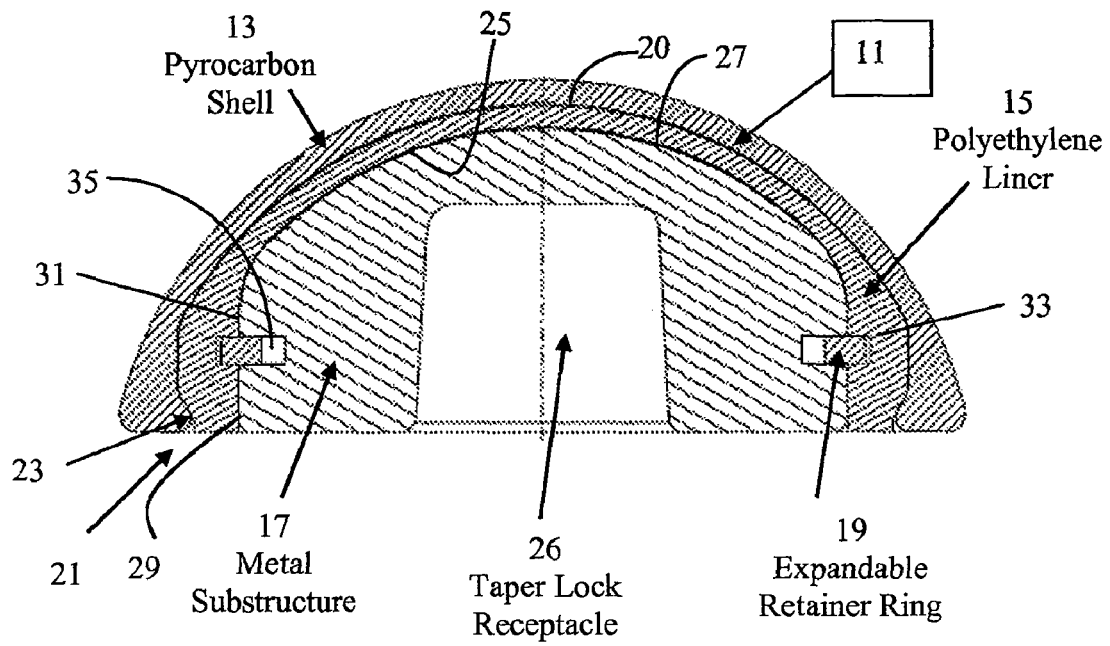
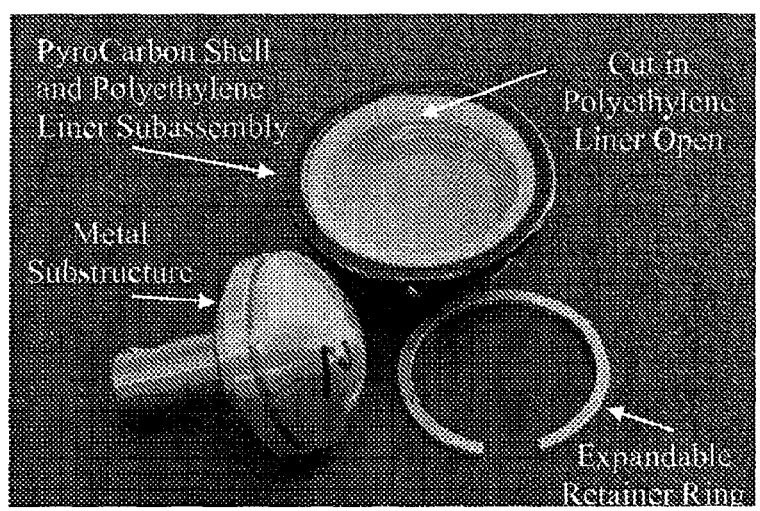
FIGURE 8A FIGURE 9. Illustration of Compressive Pyrocarbon Load Transfer
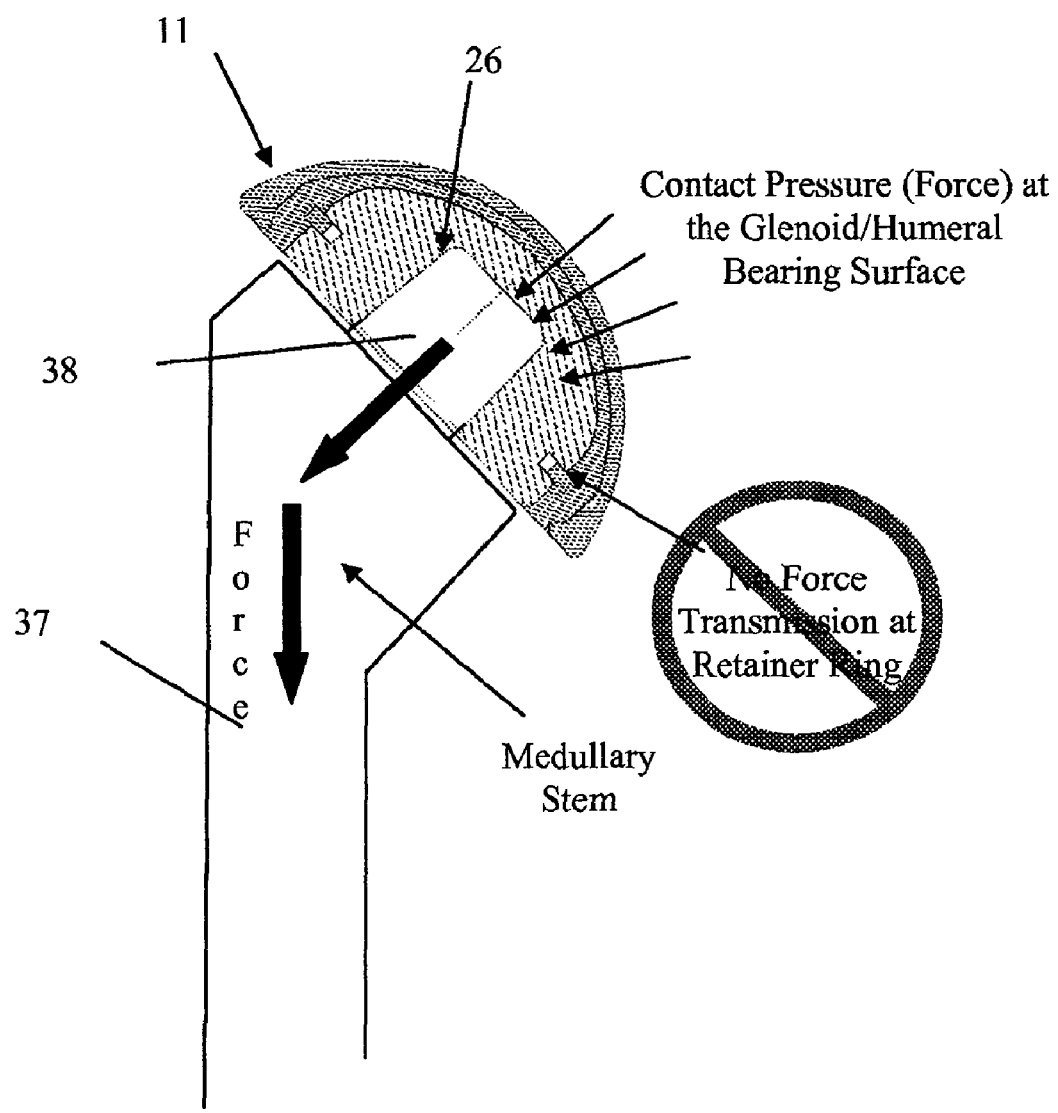

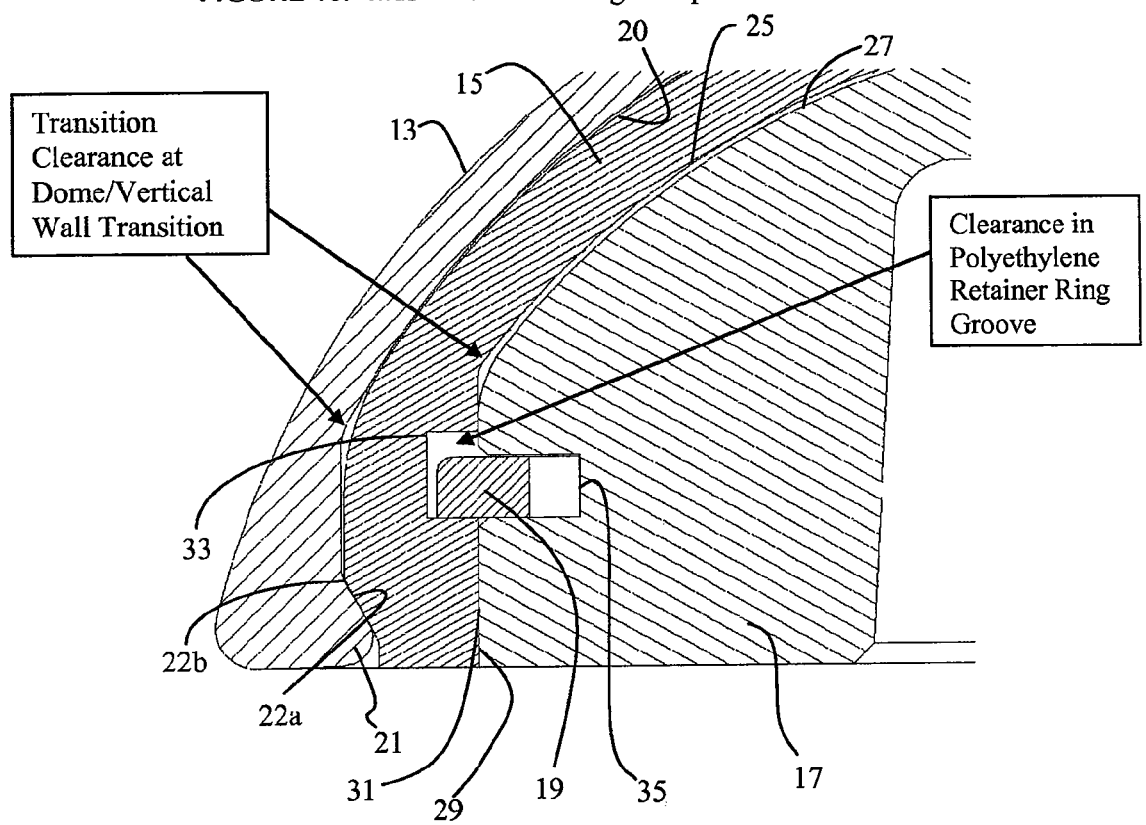
FIGURE 10. Illustration of Mating Component Clearances

FIGURE 11 Clearances Requires for Sliding Contact of Dome portions of mating parts
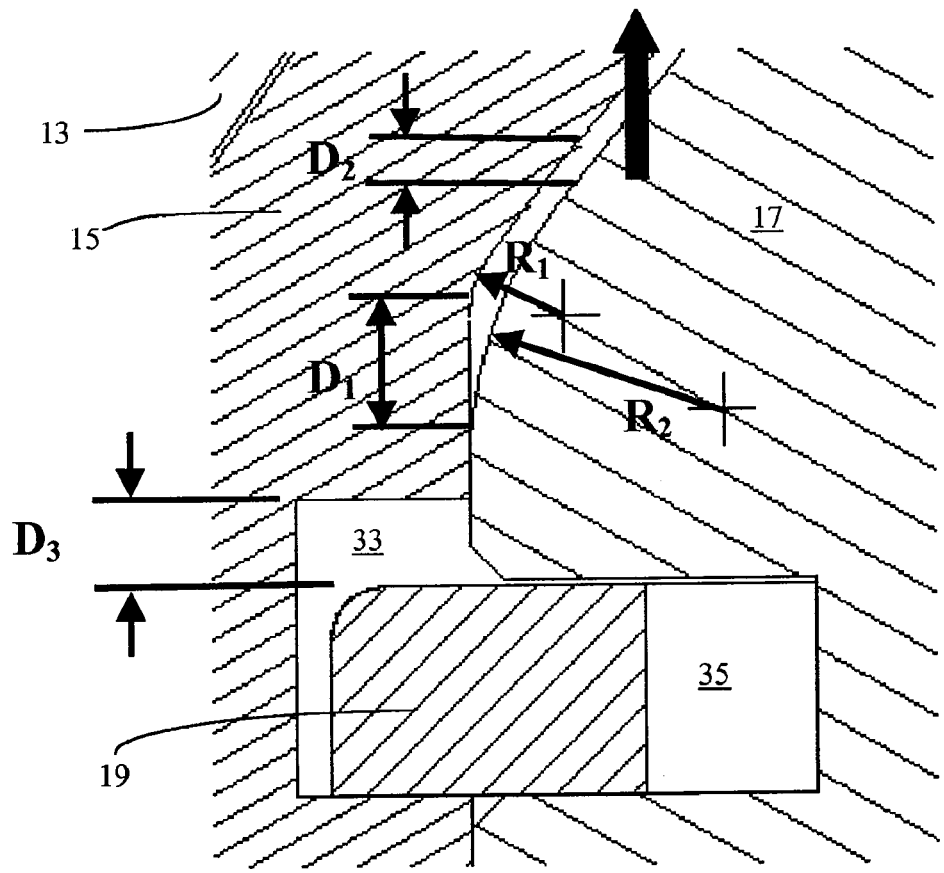
FIGURE 12. Interference Fit of Polyethylene Liner and Pyrocarbon Shell
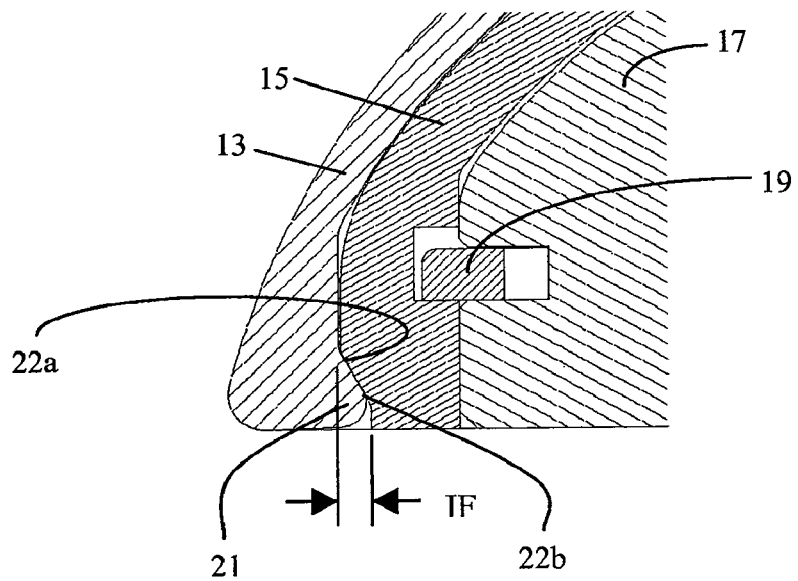

FIGURE 13A
FIGURE 13B
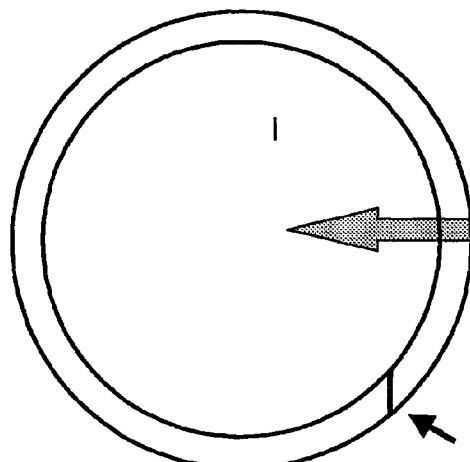
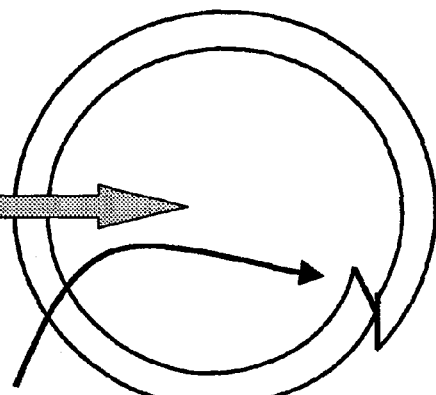
Liner Base
Separation and
Collapse
FIGURE 14A
FIGURE 14B
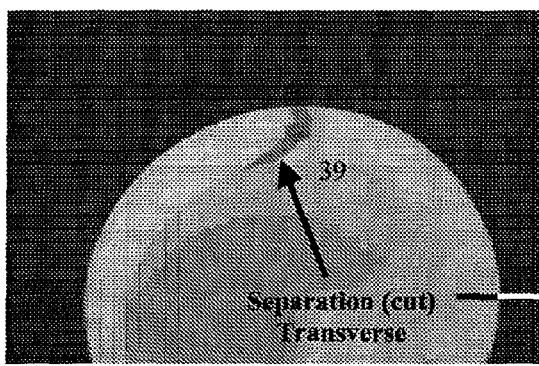
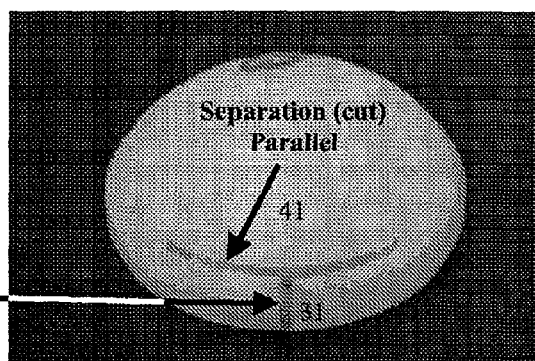

FIGURE 15 Humeral Head Dimensions
| Size Designation | W (mm) | H (mm) |
|---|---|---|
| 1 | 40 | 16 |
| 2 | 44 | 18 |
| 3 | 48 | 20 |
| 4 | 52 | 21 |
| 5 | 56 | 21 |
FIGURE 16. Thickness of Shell parts
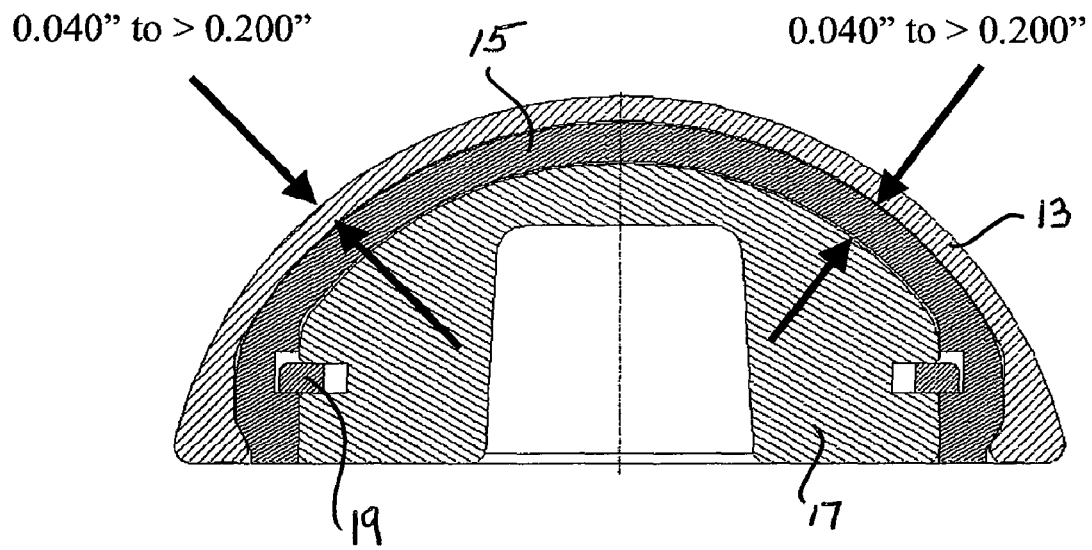

FIGURE 17. Humeral Head Component Hosting Male Portion of Taper Lock Mechanism
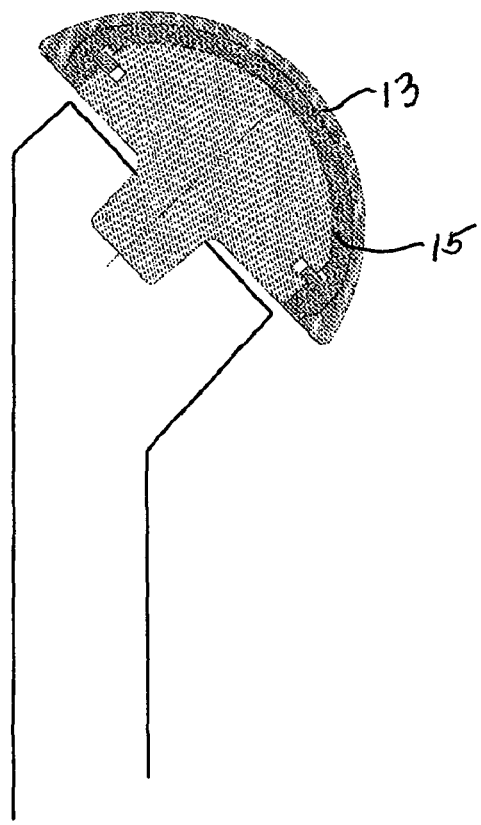
FIGURE 18 Pyrocarbon Shell in Direct Contact with Metal Substructure
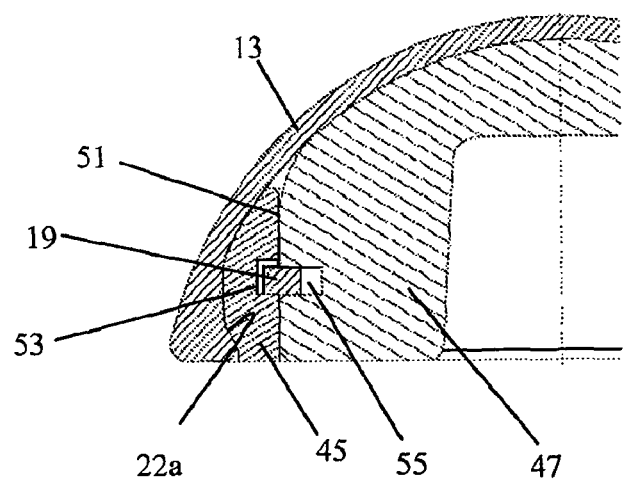

FIGURE 19
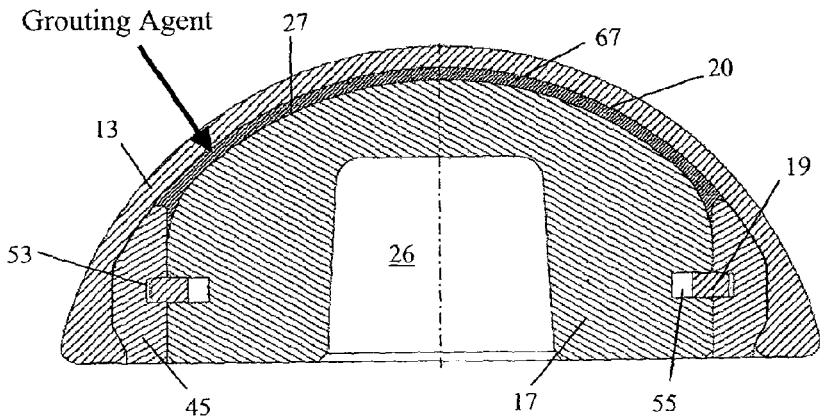
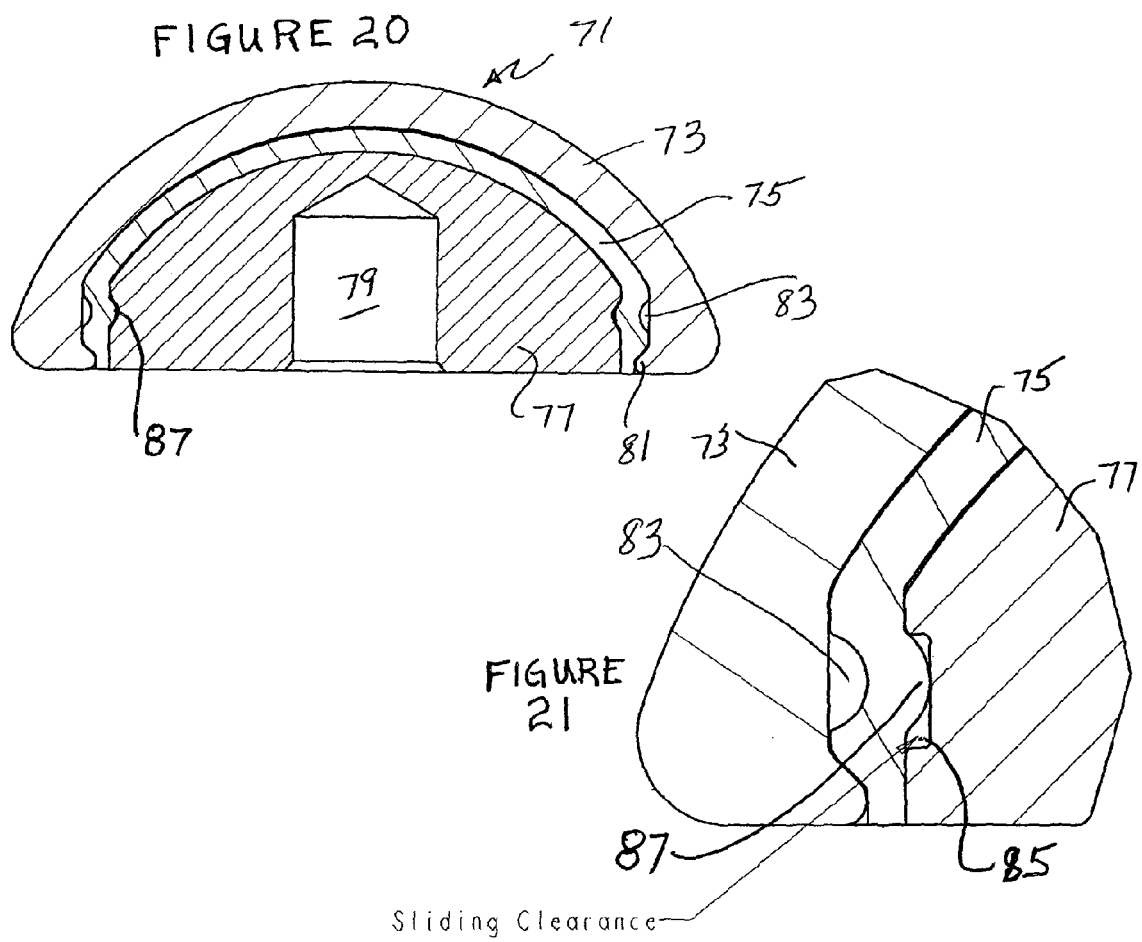

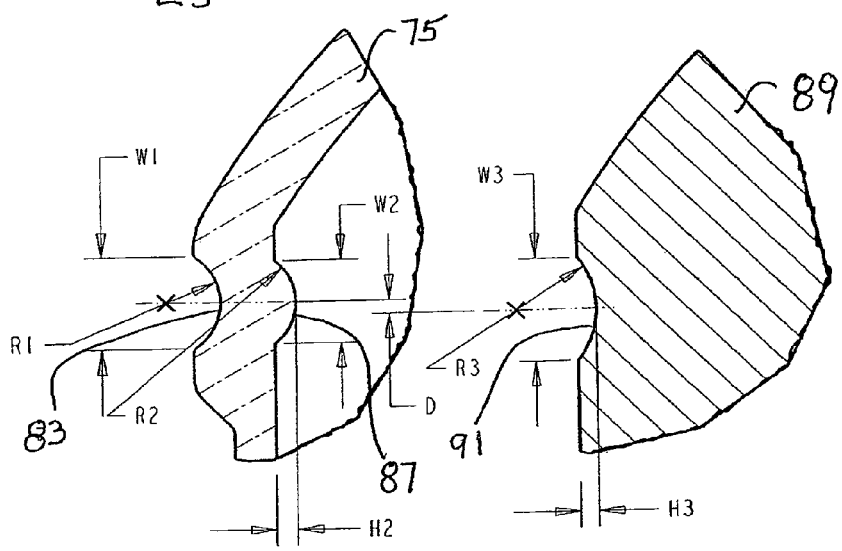
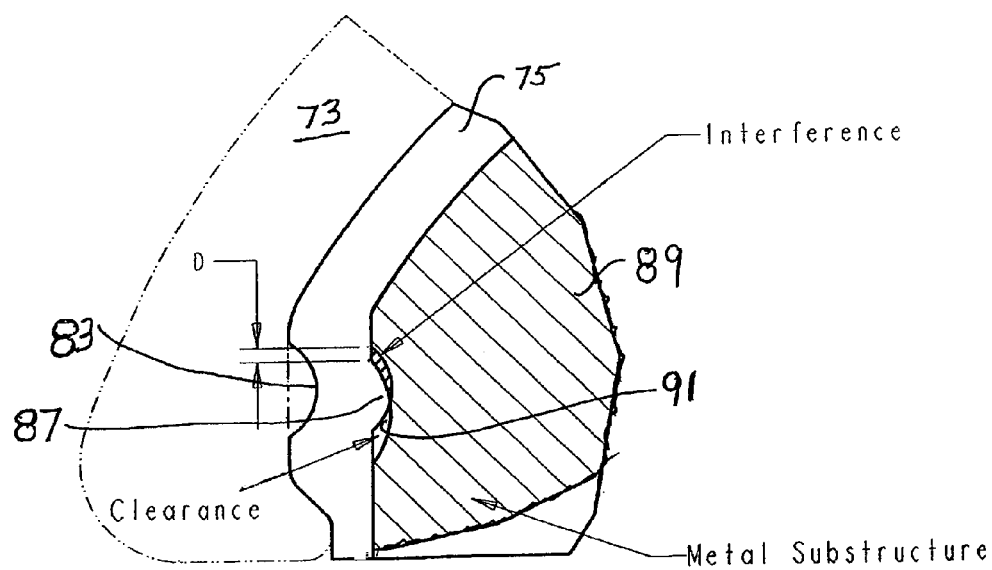

SHOULDER JOINT IMPLANT

This application claims priority from U.S. Provisional Application Ser. No. 60/867,741, filed Nov. 29, 2006, the disclosure of which is incorporated herein by reference.

BACKGROUND OF THE INVENTION

One type of shoulder joint prosthesis is called a humeral head "resurfacing" implant, and another is a humeral head "replacement" implant. Humeral head resurfacing is a conservative approach to humeral head arthroplasty and is accomplished by using a dome-shaped, thin wall shell structure to resurface the humeral head. The former implant has a fairly short central stem to achieve fixation to the humeral bone and to preserve most of the existing bone. In humeral head replacement, the entire humeral head is cut off during surgery, whereas the humeral head replacement implant has longer medullary stem to fix the implant to the humeral bone. FIGS. 1A, 1B and 1C illustrate two such implants representative of those presently in use.

As background information, the shoulder joint is formed by the head of the humerus articulating with a shallow socket called the glenoid. The glenoid is located on the lateral margin of the scapula, as shown in FIG. 2. Both the humeral head resurfacing and replacement implants can be used in total joint replacements or in hemi joint replacements. Total joint replacements typically include a polyethylene socket that replaces the glenoid as shown in FIGS. 3A and 3B.

More than half of the shoulder joint arthroplasties done in the US are hemi arthroplasties because the exposure to the glenoid is difficult; moreover, the bone mass comprising the glenoid is so limited that a glenoid replacement part may often loosen. In addition, humeral head replacement implants are more commonly used than humeral head resurfacing implants.

Presently, humeral head implants (both humeral head replacement and resurfacing implants) used in total and hemi joint replacement are made of Co—Cr alloy. However, it is now recognized that Co—Cr alloy is damaging to joint tissues (cartilage and bone) and is a shortcoming of such a hemi-arthroplasty. Pyrocarbon has been shown to be much less damaging to native joint tissues (cartilage and bone); thus, it is a better hemi-arthroplasty material than metal or ceramics, such as aluminum oxide or zirconia. Pyrocarbon is a brittle material and as such is not as strong and tough as Co—Cr alloy; thus, designs of pyrocarbon humeral head implant devices that meet the strength performance requirements are desired.

SUMMARY OF THE INVENTION

Through the use of careful engineering, it is found that pyrocarbon humeral head implants can be designed that will meet ASTM F 1378-05, Standard Specification for Shoulder Prostheses, which states that the normal joint reaction force acting on a humeral head that needs to be accommodated can be 2 times body weight. Assuming a normal body weight to be 180 lbs. the joint force acting on the humeral implant would be 360 lbs., and worst case situations could result in an even greater force on a humeral head implant. These forces can be accommodated by designs described hereinafter.

In one particular aspect, the invention provides an implant for providing a replacement articulating surface for the head of one bone member of an orthopedic joint, which implant comprises a pyrocarbon shell having an outer surface which is a section of a sphere, a concave interior surface and an open proximal base, a metal substructure having a convex distal surface and means at a proximal end thereof for securing the implant in a cavity formed at the end of a bone, and an intermediate element which is sufficiently flexible to allow its insertion axially into said open proximal base of said pyrocarbon shell and create an interference fit that prevents its withdrawal from this subassembly of shell and intermediate element, said element and said metal substructure having interengaging means which allows said metal substructure to be inserted fully into said subassembly but prevents its withdrawal therefrom, whereby forces at said joint are transferred compressively through said pyrocarbon shell to said convex surface of said metal substructure.

In another particular aspect, the invention provides an implant for providing a replacement articulating surface for the head of the humerus in the shoulder joint, which implant comprises a pyrocarbon shell having an outer convex surface which is a section of a sphere, a concave interior surface and an open proximal base, a metal substructure having a convex distal surface and means at the proximal surface thereof for securing the implant in a cavity formed at the end of a bone, and an intermediate element in the form of a shell which is sufficiently flexible to allow its insertion axially into said open proximal base of said pyrocarbon shell and create an interference fit that prevents its withdrawal from this subassembly of shell and intermediate element, said shell having a convex outer surface section which substantially abuts said interior concave surface of said pyrocarbon shell, said intermediate element having a cylindrical interior surface section and said metal substructure having a cylindrical surface section proportioned to juxtapose with that of said intermediate element, said element and said metal substructure having facing grooves in said cylindrical surfaces that align with each other when said metal substructure is fully inserted into said subassembly, and an expandable retainer that is completely received in the groove in said metal substructure that expands and resides partially in each of said facing grooves after such insertion of said metal substructure into said subassembly, whereby forces at said shoulder joint are transferred compressively through said pyrocarbon shell to said convex surface of said metal substructure.

In a further particular embodiment, the invention provides an implant that provides a replacement articulating surface for the head of one bone member of an orthopedic joint, which implant comprises a pyrocarbon shell having an outer surface which is a section of a sphere, a concave interior surface and an open proximal base, a metal substructure having a convex distal surface, a proximal cylindrical surface section and means at a proximal end thereof for securing the implant in a cavity formed at the end of a bone, and an intermediate element which has a convex domed outer surface distal section, that substantially abuts said interior concave domed surface of said pyrocarbon shell, and has a proximal cylindrical interior surface section, and which is sufficiently flexible to allow its axial insertion into said open proximal base of said pyrocarbon shell and create an interference fit that prevents its withdrawal from this subassembly of shell and intermediate element, said metal substructure being mated with said intermediate element so that its cylindrical surface juxtaposes with that of said intermediate element, and said intermediate element and said metal substructure having interengaging elements which allow said metal substructure to be inserted fully into said subassembly but prevent its withdrawal therefrom so that forces at said joint are transferred compressively through said pyrocarbon shell and said intermediate element to said convex surface of said metal substructure.

BRIEF DESCRIPTION OF THE DRAWINGS

FIG. 2 is an illustration of shoulder joint anatomy.

FIGS. 3A and B show a prior art total joint prosthesis both as a right-side view and installed.

FIG. 4 is a sketch showing representative dimensions employed to design a spherical cap for a humeral head replacement implant.

FIGS. 5 and 6 show cross-sectional views through structures that represent solid and shell forms of graphite substrates that might be employed for making a pyrocarbon humeral head replacement component.

FIG. 7 is a cross-sectional view showing one embodiment of a humeral head replacement implant embodying various features of the present invention.

FIG. 8A is a pictorial illustration of the components of the implant shown in FIG. 7 with the intermediate liner inserted into the pyrocarbon shell to create a subassembly.

FIG. 9 is a schematic illustration showing compressive load transfer of forces applied to the head at the glenoid bearing surface through the pyrocarbon shell.

FIG. 10 is a fragmentary cross-sectional view, enlarged in size, of the FIG. 7 embodiment.

FIG. 11 is a schematic view similar to FIG. 10 showing a still further enlargement.

FIG. 12 is a view similar to FIG. 10 for the purpose of illustrating the interference fit between the pyrocarbon shell and the intermediate liner.

FIGS. 13A and 13B are schematic illustrations showing the separation cut provided at the base of the polyethylene liner and its collapse at the time of insertion into the pyrocarbon shell to create the subassembly.

FIG. 14A is a top view of the intermediate liner showing the separation cut.

FIG. 14B is a perspective view of a further embodiment of such an intermediate liner where a transverse cut along a plane perpendicular to the axis element intersects with the separation cut shown in FIG. 14A.

FIG. 15 is a chart showing representative dimensions that a set of five humeral head implants might have to provide a surgeon with a choice of heads of varying size to best accommodate a patient.

FIG. 16 is a view similar to FIG. 7 which is illustratively marked to aid in the discussion of thickness dimensions for the two components of the subassembly.

FIG. 17 illustrates an alternative embodiment of the humeral head implant of FIG. 16 wherein the only change is in the metal substructure which is formed with a male extension that is received in a female cavity formed in a stem to effect the taper lock interconnection.

FIG. 18 is a fragmentary cross-sectional view similar to FIG. 10 showing an alternative embodiment of humeral head implant wherein the intermediate element is of annular shape, rather than being a complete shell which juxtaposes with the interior surface of the pyrocarbon shell throughout its entire interior surface area as in the humeral head implant illustrated in FIG. 7.

FIG. 19 is a cross-sectional view similar to FIG. 7 of yet another alternative embodiment of a humeral head implant which employs an intermediate element generally similar to that of FIG. 18 and a grouting agent which is used to fill otherwise open space between the convex domed surface of the metal substructure and the interior domed surface of the pyrocarbon shell so as to transmit compressive load through the pyrocarbon shell and grouting agent to the metal substructure.

FIG. 20 illustrates another alternative embodiment of a humeral head implant similar to that of FIG. 17 wherein the metal substructure is formed with a shallow groove that receives a protruding ring or bead on a polyethylene intermediate element to effect the locking interconnection.

FIG. 21 is a fragmentary cross-sectional view of FIG. 20 enlarged in size.

FIG. 22 is a cross-sectional view similar to FIG. 20 of yet another alternative embodiment of a humeral head implant which employs an intermediate element generally similar to that of FIG. 20 and a convex domed metal substructure wherein a groove of arcuate cross section is dimensioned and located to lock its domed surface in tight contact with that of the intermediate element so as to transmit compressive load through the pyrocarbon shell and the intermediate element to the metal substructure.

FIGS. 23 and 24 are fragmentary cross sectional views, enlarged in size, of the intermediate element and the metal substructure of FIG. 22.

DETAILED DESCRIPTION OF THE PREFERRED EMBODIMENTS

Figure 1A:
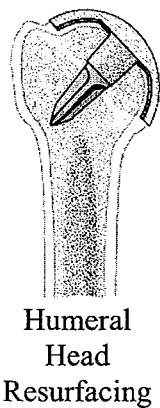
FIG. 1A is a schematic cross-sectional drawing showing a prior art humeral head resurfacing implant.
Figure 1B:
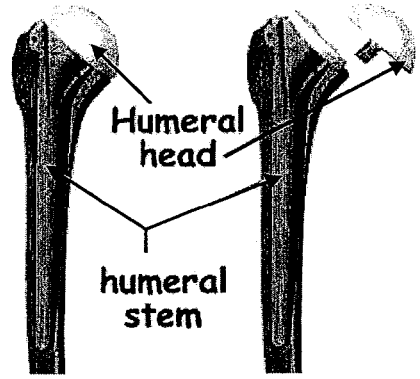
FIGS. 1B and 1C are schematic drawings showing a humeral head replacement implant installed and in exploded perspective.
Figure 1C:
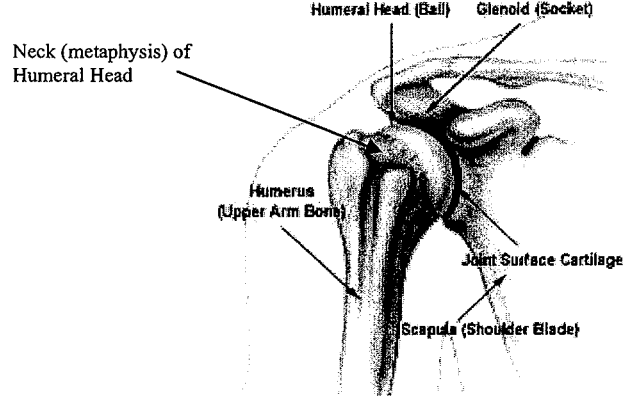

The human humeral head may be fairly well represented as a near hemisphere, i.e. a spherical cap with dimensional relationships as shown in FIG. 5. Iannotti, in *J Bone Joint Surg* (am) 74:491-500, 1992, reports that the dimensions of the human humeral head can be as large as R=28 mm, W=55.4 mm and H=24 mm.

Pyrocarbon parts are commonly made by depositing a layer of pyrolytic carbon on a graphitic substrate structure using a chemical vapor deposition (CVD) process. A fluidized bed coater is often used to apply the pyrolytic carbon coating to a graphite substrate of desired shape and dimensions. Graphite parts to be coated are levitated in the fluidized bed, which insures a continuous pyrolytic carbon coating is deposited on the substrate. Massive parts are more difficult to levitate in a fluidized bed than less massive parts; thus, it is advantageous to reduce the mass of the part to be coated as much as possible. A solid graphite substrate part in the shape of a spherical cap, as depicted in FIG. 5, with dimensions R=28 mm and W=55 mm has a volume of approximately 36.2 cc and may have a mass of approximately 64.4 grams. The mass of the part can be reduced significantly by making a thin wall shell form, rather than a solid form, as shown in FIG. 6. A graphite shell having W=55 mm, H=24 mm and shell thickness of 2 mm has a volume of approximately 7.8 cc and a comparable mass of approximately 13.9 grams, i.e. about 78% less mass than the similar solid form.

In summary, coating a substrate with substantially less mass has the following advantages: 1. Parts of less mass are more easily levitated in a fluidized bed coater. 2. The number of parts that can be coated at one time in a fluidized bed coater is often limited by the total mass of the parts to be coated, i.e., there is a maximum total mass per coater run. If individual parts have less mass, then more parts can be coated at one time, resulting in a higher efficiency per coater run. 3. Resultant coated parts having less massive graphite substrates will have reduced post-coating residual strain, which inherently results from difference between the thermal expansion coefficient of the pyrolytic carbon coating and the thermal expansion coefficient of the graphite substrate.

A humeral head replacement implant, which is made using a pyrocarbon shell as the articular (bearing) surface, should support the pyrocarbon shell with a structure that will allow it to be mounted to a medullary stem component. Ideally, the head component and the stem component are made modular to allow for assembly of different size head components with different size stem components to meet anatomic variations expected from one patient to another. A common and successful means of connecting such modular orthopedic joint implant head and stem components employs a taper lock mechanism, although other suitable frictional interconnections and such employing interference fits, as known in this art, may be used. Supporting a pyrocarbon shell that is providing the articulating surface upon a metal substructure provides the ability to use such a taper lock mechanism or the like to join the pyrocarbon-surfaced head component to a modular metal stem is preferred. However, an integral metal substructure which includes a stem is an alternative but is less desirable.

Pyrocarbon is a brittle material, and as with other brittle materials, it is much stronger in compression than tension. By designing a system for attaching a pyrocarbon shell to the metal substructure that insures that the pyrocarbon bearing surface is placed in compression when transmitting loads between the pyrocarbon shell structure and the metal substructure, the effective employment of an articular pyrocarbon surface in an implant for use in an arthroplasty is facilitated. The design of the attachment mechanism for joinder of the pyrocarbon shell to the metal substructure should also insure that, once assembled, the assembly will not come apart, i.e. disassemble.

Shown in FIG. 7 is one embodiment of a design of a head 11 that effects the transmission of joint forces in compression through a pyrocarbon shell 13 and through an intermediate element 15, such as a polyethylene liner, to a central metal substructure 17. Retaining means, such as a collapsible-expandable, split ring retainer 19, permanently locks the assembled components together so they will not disassemble. The metal substructure 17 preferably contains a female cavity 26 in its proximal flat surface to interconnect the head with a modular stem.

As seen in FIG. 7, the intermediate element 15 is a shell-shaped overall liner structure that might be machined or molded of polyethylene or other suitable biocompatible polymer or copolymer; it fits between the metal substructure 17 and the pyrocarbon shell 13, and it has an outer convex surface which juxtaposes with the entire concave inner surface 20 of the pyrocarbon shell. The pyrocarbon shell 13 has an inward protruding lip 21 at its base that engages a reduced portion 23 of the polyethylene liner to form an interference fit (IF) as shown. The central inner surface 25 of the polyethylene liner 15 and the central surface 27 of the metal substructure 17 are dome shaped at their tops or distal regions, but have rectilinear walls 29, 31 at their base peripheries. The rectilinear walls are preferable right circular cylindrical surfaces. Facing grooves 33, 35 are located in the polyethylene liner and metal substructure, respectively, to house the flat split ring retainer 19 which is the preferred retaining means; however, other retaining mechanisms may alternatively be used that would prevent disassembly.

The components are assembled as follows. First, the polyethylene liner 15 is axially inserted into the pyrocarbon shell 13 through the circular opening in the base at the rim provided within the circular lip 21 to form a subassembly. The facing surfaces are juxtaposed through their entire surface areas and have a frictional fit which prevents any relative rotation. Just interior of the lip 21, the pyrocarbon shell is formed with an oblique surface 22a (see FIG. 10) which frictionally abuts a facing surface 22b on the intermediate element and assures a tight fit of the respective juxtaposed concave and convex surfaces by the axial force vector that results. The retainer 19 is preferably a metal split ring and that can be expanded to slide over the metal substructure surface until it springs back slightly at the retainer ring groove 35 cut into the metal substructure where, in its relaxed condition, it will protrude outward for a distance equal to about one-half its width. The depth of the retainer ring groove 35 in the metal substructure is slightly greater than the width of the retainer ring 19; such allows the split retainer ring 19 to be compressed (i.e. collapsed) so as to seat completely in the retainer ring groove and not extend past the outer cylindrical wall 31 of the metal substructure component, in which condition the metal substructure 17 is slidably inserted into the polyethylene liner 15 of the pyrocarbon shell-liner subassembly. The manufacturing tolerances are such that the diameter of the cylindrical base section of the metal substructure 17 is just slightly greater than the diameter of the corresponding interior cylindrical base surface of the intermediate element 15 so there will be a press-fit that is accommodated by the resilience of the polymeric liner material.

As the metal substructure 17 is pressed deeply into the polyethylene liner 15, the retainer ring 19 reaches the retainer ring groove 33 in the polyethylene liner and expands to its original relaxed size, so it now resides partially both in the groove 33 in the polyethylene liner and in the groove 35. The width of the expandable flat retainer ring 19 is greater than the depth of the retainer ring groove 33 in the polyethylene liner, and the ring is sized so that, in its relaxed condition, it resides about one-half in both grooves in the metal substructure 17 and the intermediate element 15. The dimensions of the intermediate element/liner 15 and the metal substructure 17 and the locations of the two grooves are such that, when the split ring 19 expands to partially enter the groove 33, the dome surfaces 25, 27 of the two components are very close to the full insertion position where they are abutting or at least very nearly abutting across their entire surface areas that lie distal of transition regions where the respective dome and cylindrical surface sections meet.

Figure 8B:
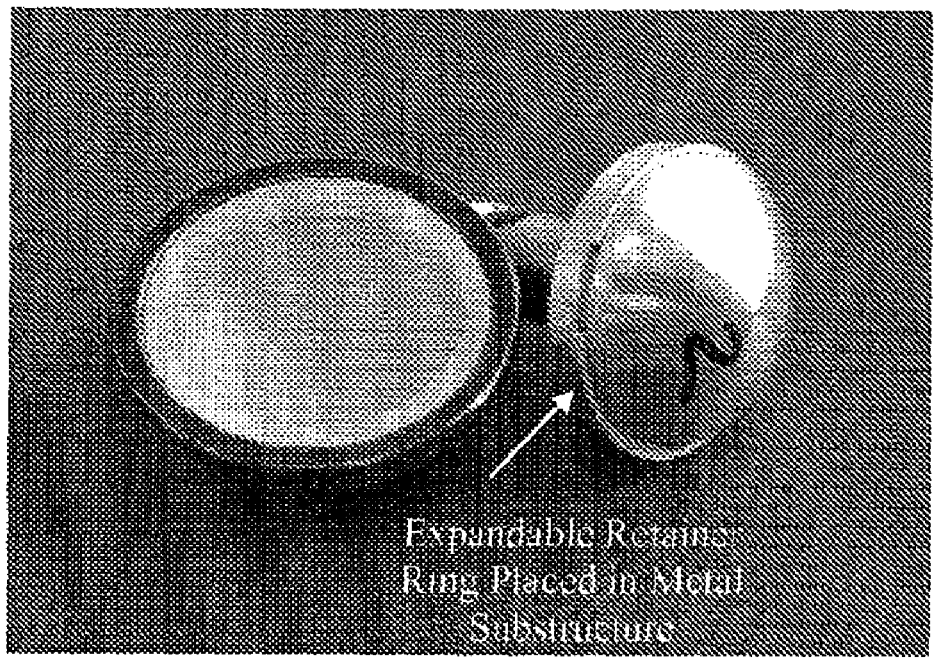
FIG. 8B shows the components of FIG. 8A with the expandable retainer ring in place in the groove on the metal substructure.

This assembly process is shown step-by-step in FIGS. 8A-E. FIG. 8A shows the component parts after the polyethylene liner 15 has inserted into the pyrocarbon shell 13 to form the initial subassembly. A cut has been placed in the base of the polyethylene liner which is discussed hereinafter, and an assembly tool is mated with the metal substructure 17. FIG. 8B shows the split ring retainer 19 placed in the groove

Figure 8C:
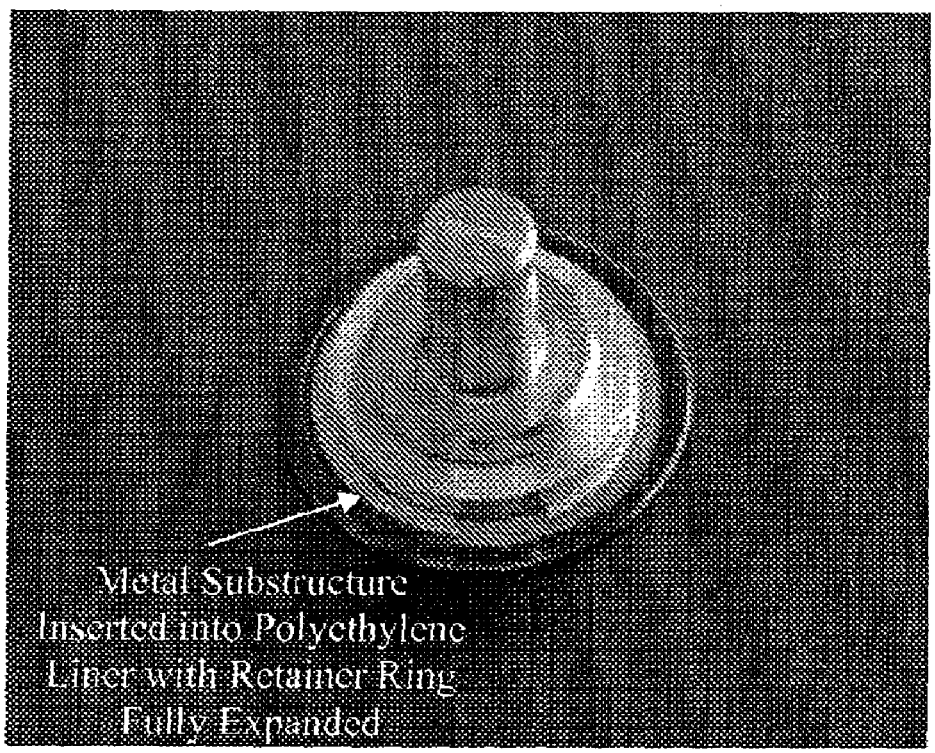
FIG. 8C shows the components of FIG. 8B aligned with the metal structure partially inserted into the subassembly, but with the retainer ring still in its fully expanded condition. The stem which is shown attached to the metal substructure is a tool for supporting the humeral head implant in a test apparatus and is not shaped for insertion into a cavity provided in a humerus.
Figure 8D:
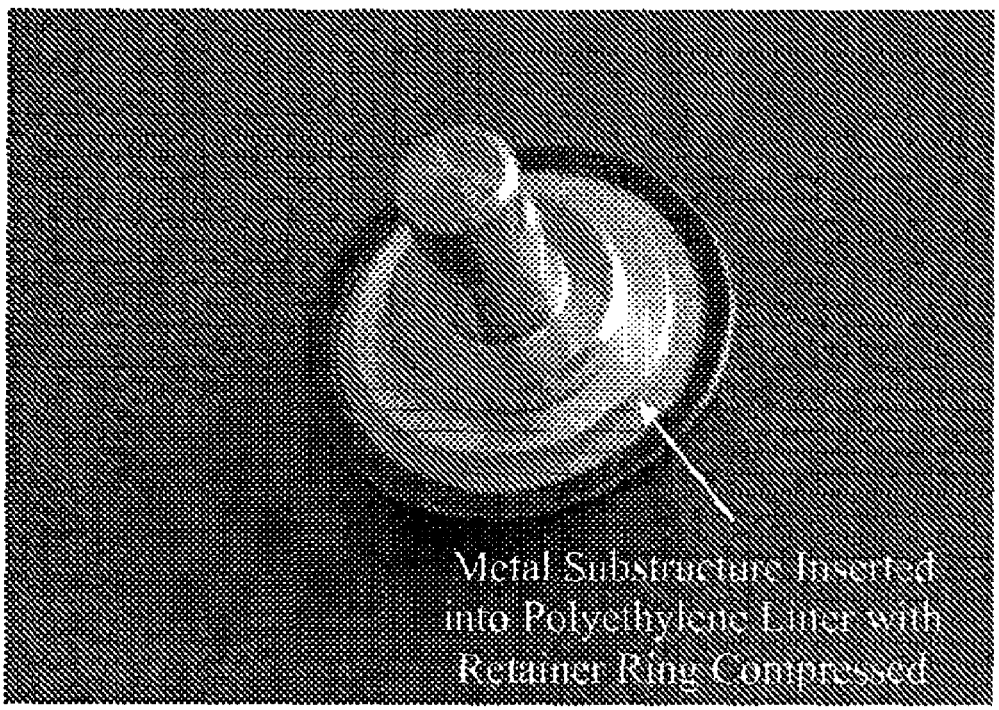
FIG. 8D is a view similar to FIG. 8C with the retainer ring compressed and the metal substructure inserted further into the subassembly.
Figure 8E:
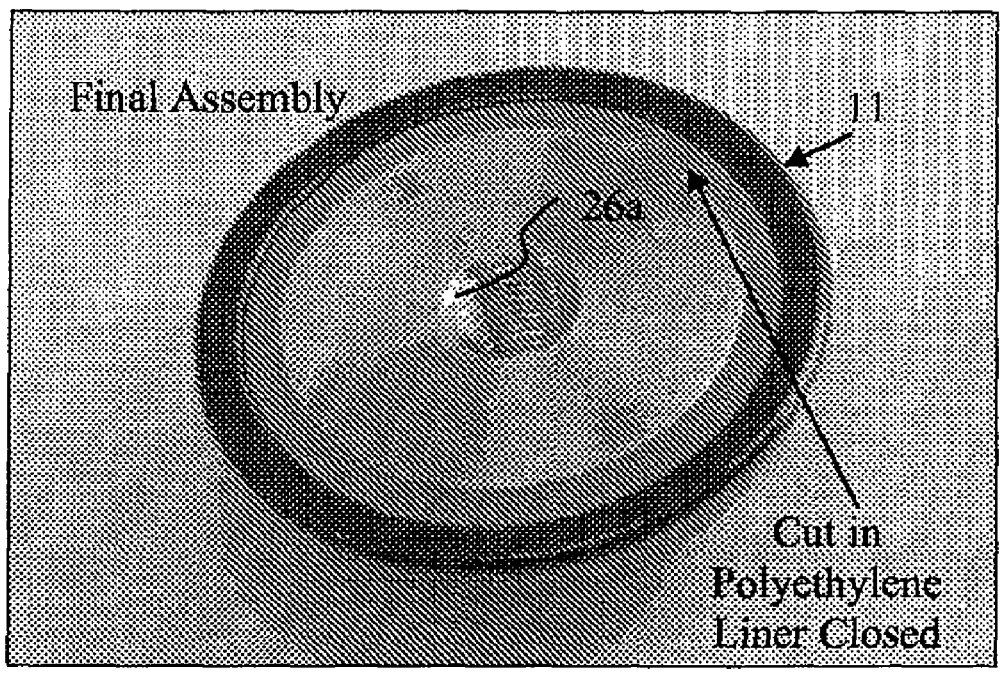
FIG. 8E is a view showing the fully assembled humeral head implant as seen in FIG. 8A with the test tool removed.

35 of the metal substructure 17 but not yet compressed. FIG. 8C shows the metal substructure 17 partially inserted into the pyrocarbon shell/polyethylene liner subassembly with the retainer ring 19 still in its uncompressed (relaxed) condition. FIG. 8D shows the metal substructure being inserted into the polyethylene liner as a press fit with the retainer ring now compressed (collapsed). FIG. 8E shows the final, assembled humeral head replacement implant 11. In FIG. 8E, a threaded hole 26*a* is shown as a female cavity, instead of a preferred taper lock receptacle; its purpose is to facilitate attachment to the assembly tool used to carry out mechanical testing on prototypes.

An important feature of the design of the humeral replacement head 11 is that the pyrocarbon material that constitutes the articular load-bearing surface of the device will always be transmitting loads in compression and not in tension. Pyrocarbon is a brittle material and as such is much stronger in compression than in tension. The objective, as illustrated schematically in FIG. 9, is to achieve compressive load transfer between the glenoid/humeral pyrocarbon head bearing surface (through the polyethylene liner 15) and the metal substructure 17. The metal substructure 17 then transfers load to the humerus through a medullary stem 37 which might be integral therewith, but preferably, transfer is through the surface-to-surface contact between the receptacle 26 and a male post 38 at the end of the stem 37 (which effects a taper lock interconnection between a modular stem 37 and the metal humeral head substructure 17). The design of the components is such that loading at the orthopedic joint is not transferred from the pyrocarbon shell bearing surface to the metal substructure through the retainer ring 19. Load transfer via the split ring retainer 19 would concentrate all joint loading at the location of such interengagement and result in high stresses that could potentially cause damage to the polyethylene liner and possibly even damage to the flat retainer ring. Furthermore, such load transfer at the location of the retainer ring 19 would mean that compressive load transfer is not occurring through the relatively large surface area of the pyrocarbon shell 13 to the polyethylene liner and then to the metal substructure at the approximate points in the joint where the bearing surfaces contact each other. Such prospective load transfer at the location of the retainer ring, rather than at the points of joint bearing surfaces contact, could result in undesirable tensile stress in the pyrocarbon shell and ultimate debilitation.

FIG. 10 illustrates the four component parts of the humeral head implant 11 (pyrocarbon shell 13, polyethylene liner 15, metal substructure 17 and retainer ring 19) disposed in assembly when the ring has just entered the groove 33 and before there is intimate contact along the domed bearing surfaces of the liner and metal substructure. In actual practice, achieving precise, intimate contact along the entire dome surface area of all three parts of the humeral head implant is not possible due to manufacturing tolerances. Specific attention is thus given to the geometries (shapes) of the pyrocarbon shell 13, the polyethylene liner 15 and the metal substructure 17 to insure compressive contact between these three parts occurs at the approximate locations aligned with the locations of loading between the articular surfaces of the humeral head and the glenoid. Contact of the domed concave surface of the pyrocarbon shell/polyethylene liner subassembly against the convex surface of the metal substructure (so that forces being applied at the genoid/humeral head articular surface are transferred in compression) is achieved by providing certain clearances such that allow the mating parts to slide freely one within the other near the end of the insertion of the metal substructure; as a result, force-transferring contact occurs substantially only at the domed surface portions of each component. It is by avoiding premature contact at the locations where the domed surface of each part transitions to its cylindrical surface portion that this desirable objective is achieved.

Axial clearance space is also provided in one of the grooves, preferably the polyethylene liner groove 33, by increasing its axial thickness in order not to impede travel of the metal substructure into the polyethylene liner sufficiently to seat its domed surface 27 in abutting contact with the interior surface 25 and thus achieve compressive contact along the mating dome surface portions. Thus, compressive load transfer at the bearing surfaces between the pyrocarbon shell 13 to the polyethylene liner 15, and then at the bearing surfaces between the polyethylene liner and the metal substructure 17 is achieved by provision of similar suitable clearances at both sets of transition regions where the concave or convex generally spherical surfaces of transition to their respective cylindrical surfaces, as illustrated in FIG. 10.

One design for achieving the aforementioned desired clearances at these transition regions from the cylindrical surface portions to the dome surface portions of each of the three mating parts is to use two different blend radii at each of the two pairs of facing transition regions; one such arrangement is illustrated in FIG. 11. FIG. 11 shows the point of the assembly procedure where the split ring 19 has just expanded radially outward to enter the groove 33 in the liner; to reach its final abutting position, the metal substructure must travel an axial distance of $D_2$ in the direction of the bold black arrow. The view emphasizes that, when the blend radius $R_2$ between the two surfaces of the metal substructure 17 is greater than the blend radius $R_1$ for the transition of the interior surfaces of the polyethylene liner 15, there will be provided an amount of axial clearance $D_1$ which is greater than the distance of travel $D_2$ that is required to completely close any tolerance-related gap between the dome portions of the metal substructure 17 and the polyethylene liner 15. FIG. 11 also illustrates that the liner groove 33 clearance $D_3$ is also preferably greater than $D_2$ so that protruding ring 19 will not interfere with the further sliding movement needed to seat the dome portions of the two parts. Once insertion is complete, the press fit between the cylindrical surfaces 29 and 31 will tend to maintain this assembled orientation. The same clearance principles, i.e. blend radii of different curvatures, are used to assure there is tight contact between the juxtaposed dome portions of the polyethylene liner 15 and the pyrocarbon shell 13.

It should be understood, however, that the use of blend radii having different radii of curvature as depicted in FIG. 11 is not the only means to achieve clearance so that the pyrocarbon shell, polyethylene liner and metal substructure parts can slide relative to one another to achieve such a compressive load-bearing layered structure. Chamfers and other clearance-producing means can be used to allow the parts to slide together sufficiently to form a compressive load-bearing, layered structure.

In summary, the function of the retainer ring 19 is to prevent the metal substructure 17 from being pulled out of the polyethylene liner 15; other suitable retaining mechanisms as mentioned hereinafter may alternatively be used. It is important the forces acting on the humeral head implant during load-bearing function are transferred compressively in the pyrocarbon shell to the metal substructure, and in doing so in this embodiment, they sandwich the polyethylene liner between the shell and the metal substructure. As a result, the polyethylene liner is forced against the facing surface of the pyrocarbon shell 13. During load-bearing function, the retainer ring 19 carries no load because it can freely move axially in the groove 33 due to clearance provided by the axially wider groove. While the primary force acting on the humeral head implant serves to force the assembled parts together during load-bearing function, the combination of the retainer ring and the interference fit at the base between the polyethylene liner 15 and pyrocarbon shell 13 serve to lock the parts together so that they will not disassociate during shipping or handling of the device during surgery. The locking mechanism further insures the parts will not disassociate as a result of some unexpected joint function that might tend to try to pull the metal substructure 17 out of the polyethylene liner/pyrocarbon shell subassembly.

As best seen in FIG. 12 below, in this embodiment, an interference fit (IF) occurs between the pyrocarbon shell 13 and the polyethylene liner 15 at the base of the shell. The size of the interference fit necessary to capture the polyethylene liner in the pyrocarbon shell could be a small as about 0.010"; however, it could be as great as about 0.050" or even slightly larger. The polyethylene liner 15 is a semi-rigid structure that can be press fit into the pyrocarbon shell if the IF is small, e.g. in the range of about 0.010" to 0.015". If the IF is large, e.g. about 0.050", it may not be possible to press fit the polyethylene liner into the pyrocarbon shell without likely fracturing the pyrocarbon shell. To avoid such a possibility, a generally radial but oblique separation (cut) 39 (see FIGS. 13A and 14A) can be provided in the base of the polyethylene liner to allow this base section to collapse on itself, thus making it possible to relatively easily deform the polyethylene shell, as shown in the illustration in FIG. 13B, so it can be inserted into the pyrocarbon shell without damaging the pyrocarbon shell. To further allow the polyethylene liner base to easily collapse during insertion into the pyrocarbon shell, an additional intersecting separation (cut) 41 can be provided in the shell parallel to the base plane of the shell as shown in FIG. 14B so the oblique separation (cut) 39 and the cut 41 parallel to the base plane intersect. The two base portions of the polyethylene liner at this intersection will then even more freely collapse. Following its insertion into the pyrocarbon shell 13, the resilient polyethylene liner 15 will regain its original, un-collapsed shape, and the separations in the polyethylene liner will be closed once the metal substructure 17 has been pressed into the polyethylene liner of the subassembly. The entire assembly will then cooperate to achieve both its compressive load-bearing function and will resist disassembly without any adverse effect due to the presence of the separations in the polyethylene liner.

FIG. 15 is a chart that presents a range of humeral head dimensions corresponding to the dimensions marked in FIG. 4. These represent sizes that are considered to be most useful for a surgeon to have available in a clinical setting.

The thickness of each of the domed portions of the pyrocarbon shell 13 and polyethylene liner 15 may vary from about 0.040" to about 0.200" or slightly greater. Such is diagrammatically shown in FIG. 16. As the thicknesses of the domed portions of pyrocarbon shell 13 and polyethylene liner 15 increase for a head of one particular size designation, the size of the metal substructure would be proportionately reduced. It is possible that the thicknesses of the domed portions of the pyrocarbon and polyethylene parts might grow to such an extent that a requisite reduction of the size of the metal substructure might no longer leave sufficient space to reasonably accommodate a taper lock or other such receptacle 26. Should such occur, a taper lock or other such interconnection arrangement could be constructed by simply reversing the parts, i.e. providing a male plug portion on the humeral head metal substructure and a female receptacle in the stem, as shown in FIG. 17.

Shown in FIG. 18 is an alternative embodiment embodying various features of the invention in which the pyrocarbon shell 13 is in direct contact with the convex dome of the metal substructure 17. The same general principles described for the pyrocarbon shell/polyethylene liner/metal substructure design apply to this alternative embodiment. In this embodiment, an intermediate element 45 is used which is an annular liner that occupies only a base region of the pyrocarbon shell 13. It again has an interference fit with the inwardly protruding lip 21 on the pyrocarbon shell 13 and would frictionally engage the oblique surface 22a of the pyrocarbon shell and the lower region of the concave interior dome surface 20. A metal substructure 47 is formed with a longer cylindrical surface or wall 51 which has a similar groove 55 in which the split ring retainer 19 resides in compressed form during the installation assembly, and the intermediate element 45 includes a groove 53 dimensioned as previously described with regard to the liner groove 33. As can be seen from FIG. 18, the final assembly of the metal substructure leaves its convex domed surface 57 in contact with the interior concave dome surface 20 of the pyrocarbon shell.

FIG. 19 shows a further alternative embodiment which includes various features of the invention in which a grouting agent 67 is placed between the domed sections of the pyrocarbon shell 13 and the metal substructure 17. The design uses the annular polyethylene intermediate element 45 just described and the split ring retainer 19. However, in this design the metal substructure 17 and the annular intermediate element 45 are proportioned such that, when the parts are assembled, an open space remains between the inner concave domed surface portion 20 of the pyrocarbon shell and the convex domed surface portion of the metal substructure 27. During assembly, the annular polyethylene intermediate element 45 is first assembled with the pyrocarbon shell 13 where it is positioned at its base by the engagement of complementary surfaces. The retainer split ring 19 is then placed in the retainer ring groove 35 in the metal substructure 17. At this point, a metered amount of a fluid grouting agent 67 is introduced which, in a short period of time, will set to a semi-rigid or rigid condition; the grouting material is deposited centrally of the inside domed surface 20 of the pyrocarbon shell 13. Then, the metal substructure 17 with the retainer ring 19 compressed in its retainer ring groove 35 is pressed into place until the split ring retainer expands to partially enter the groove 53 in the annular polyethylene liner 45. During the insertion process, the grouting agent 67 remains fluid and is forced by the convex dome portion of the advancing metal substructure 17 to fill the entire space between the concave domed surface 20 of the pyrocarbon shell 13 and the convex domed surface 27 of the metal substructure. The grouting agent 67 then sets to form a semi-rigid or rigid material which is capable of transferring compressive load through its body between the pyrocarbon shell and the metal substructure 17. One major advantage of the use of such a grouting agent 67 is that the need to hold close tolerances is substantially relaxed as the grouting agent will totally fill the void space and upon hardening provide an effective transfer of compressive stress from the pyrocarbon shell.

Shown in FIG. 20 is still another embodiment of a design for a head 71 that will transmit joint forces in compression through a pyrocarbon shell 73 and an intermediate element 75, such as a polyethylene liner, to a central metal substructure 77. The metal substructure 77 preferably contains a female connector 79, such as a cavity 79, that will receive a male connector in a standard taper lock connection. Similar to the pyrocarbon shells hereinbefore described, the shell 73 has an inwardly protruding lip 81 at its base.

The intermediate element 75 has an exterior shape similar to that of the polyethylene liner 15 previously described which mates with the interior contour of the pyrocarbon shell 73 after it has been axially inserted thereinto as described hereinbefore. The juxtaposed facing surfaces have a frictional fit that prevents any relative rotation. The exterior of the intermediate element 75 has an angled wall that is juxtaposed with the oblique wall of the pyrocarbon shell 73 created by the inwardly-protruding lip 81, and this creates the interference fit therebetween as described in detail hereinbefore. Strategically positioned above this angled wall, in the exterior cylindrical surface of the intermediate element 75, is an arcuate recess 83 of a predetermined shape that encircles the entire intermediate element and serves a purpose explained in detail hereinafter.

In the head 71, interengagement between the pyrocarbon shell/intermediate element subassembly and the metal substructure 77 is through two interengaging elements provided in the metal substructure 77 and the intermediate element 75 that are located in the two juxtaposed cylindrical surfaces. As best seen in FIG. 21, the cylindrical surface of the metal substructure is provided with a shallow groove 85, which is preferably of a substantially rectangular cross section. The facing interior cylindrical surface of the intermediate element 75 is provided with an arcuate bead 87 which is preferably continuous for 360 degrees encircling the cylindrical surface, although interruptions could be provided if desired at various locations. The cross section of the bead 87 is that of a segment of a circle defined by a chord of a length less than the length of the rectangular groove 85. The height of the bead is preferably about equal to the depth of the groove 85. As can be seen in FIG. 21, the bead 87 is directly axially aligned with the encircling arcuate recess 83.

When the metal substructure 77 is inserted axially into the subassembly of the polyethylene liner 75 and the pyrocarbon shell 73, the cylindrical wall of the metal substructure will slide along the cylindrical wall of the polyethylene liner until the convex dome surface reaches the arcuate bead 87. At this point, the region of the polyethylene liner 75 lying between the surface of the bead 87 and the interior surface of the encircling recess 83 is forced radially outward in elastic deformation by the cylindrical surface of the metal substrate. The relief provided by the encircling recess 83 provides a region into which the polymeric material can move without undergoing plastic flow. Further insertion of the metal substructure to the position shown in FIG. 21 completes the assembly, and in this assembled condition, the polyethylene liner 75 will return to its original shape, with the bead 87 being received within the shallow groove 85. As can be seen, the corner of the flat transverse wall of the groove 85 creates a tight locking arrangement that prevents the metal substructure 77 from being withdrawn; thus, this arrangement serves the same purpose as the retainer ring in the various other embodiments of implantable heads described hereinbefore. The location of the groove 85 on the surface of the metal substructure 77 is such that there is clearance that would allow some sliding of the metal substructure 77 further into the subassembly. This avoids the need to hold tight tolerances, as slight relative axial movement between the juxtaposed cylindrical surfaces of the metal substructure and the polyethylene liner can occur when a load is being transmitted to the implanted head to ensure there will be good contact between the juxtaposed convex/concave domed surfaces.

FIGS. 22, 23 and 24 are fragmentary views of yet another humeral head implant employing a pyrocarbon shell 73 and a polyethylene intermediate element 75 that have essentially the same construction as that described with regard to FIGS. 20 and 21. However, as best seen in FIG. 24, instead of using a metal substructure 77 with a shallow groove 85 of rectangular cross-section, a metal substructure 89 is employed which has a shallow arcuate cross-section groove 91 provided in its exterior cylindrical surface, which is positioned at a location such that of the rectangular cross-section groove 85 is not directly axially aligned with the arcuate bead 87.

The final assembly procedure is similar to that just described with respect to the head 71. The metal substructure 89 is inserted axially into the subassembly with its cylindrical outer surface sliding against the cylindrical inner surface of the polyethylene liner 75. Again, when the domed surface of the metal substructure 89 engages the bead 87, the region of the intermediate element 75 between the bead and the aligned recess 83 is forced radially outward in elastic deformation. As described hereinbefore, continuing axial insertion results in the distal portion of the cylindrical surface of the metal substructure 89 passing the proximal end of the bead of the intermediate element 75, and the bead 87 begins to expand into the arcuate groove 91 on return to its original shape in the shallow arcuate groove provided in the surface of the metal substructure. However, the shape and the location of the groove is such that, before the leading or distal edge of the arcuate groove 91 has cleared the bead 87, the convex domed surface abuts the interior concave domed surface of the polyethylene liner 75. In this position, the length of the region of interference is less than one-half the length of the chord length of the bead. The result is the arrangement depicted in FIG. 22 wherein the proximal portion of the bead 87 has returned to near its original shape being received in the proximal region of the arcuate groove 91 where there is ample clearance; however, there is interference between the bead and the confining surface of the distal portion of the shallow arcuate groove 91. This interference results in compression of the polyethylene material with the ultimate result that the returning polyethylene bead is effectively camming the dome surface of the metal substructure 89 into tight engagement with the interior concave dome surface of the polyethylene liner 75. The force which was required to deform the polyethylene and the geometry of the interfering components serves to provide this camming action which thrusts the dome of the metal substructure against the interior concave surface of the polyethylene liner. The clearance at the distal end of the groove 91 provides some room for deformation of the bead 87, in addition to that provided by the aligned encircling recess 83, when the polyethylene liner attempts to return to its original shape.

The reference numbers that are provided in FIGS. 22, 23 and 24 can be used to more particularly specify the relative dimensions and locations. It can be seen from FIGS. 23 and 24 (which are aligned as they would be axially located in the assembled condition) that the centers of the curvature of the bead and the recess are arranged so their radii R1 and R2 lie on the same line, perpendicular at the centerline of the head implant. The alignment of the shallow groove 91 is such that its radius R3 is centered on a parallel line displaced therefrom by the distance D. As a result, the distance D, as can be seen in FIG. 22, defines essentially the extent of the region of interference (see dotted outline) in the assembled head wherein the polyethylene polymeric material is compressed against the distal arcuate surface section that defines the groove and creates the camming action that thrusts the domed convex surface of the metal substructure into tight interengagement.

Generally, by pyrocarbon shell is meant a layered structure formed of medical grade pyrolytic carbon deposited on all surfaces of a graphite substrate. Intermediate element or liner means an annular or complete liner that may be made of polyethylene or any suitable biocompatible material that can be inserted into the pyrocarbon shell by means of its deforming to pass an inwardly protruding lip on the pyrocarbon shell. It may be made of a semi-rigid material, such as polyethylene, or even a flexible metal structure that can be deformed as a result of the inclusion of separations or slots in order to insert it into the pyrocarbon shell. By metal substructure is meant any biocompatible metal having suitable strength properties to transmit load from the head portion of the implant to the stem portion of the implant. Certain titanium alloys and CoCr alloys are two examples of suitable materials. By grouting agent is meant an elastomer, e.g. silicone elastomer, or a hardened cement or polymer composition, e.g. polymethylmethacrylate bone cement or an epoxy resin material which is suitably biocompatible. By stem component is meant a suitably shaped structure designed to interfit within a cavity formed in the proximal end of the humerus, which is made of a biocompatible metal having suitable strength properties, such as titanium alloys and CoCr alloys.

Prototype devices of each of the three embodiments depicted in FIGS. 7, 18 and 19 have been produced and tested in the laboratory. Appropriate mechanical testing has shown that all three embodiments are capable of effectively transmitting loads applied to the pyrocarbon shell that are, at a minimum, 2.8 times the 360 lbs. specified in ASTM F 1378-05, Standard Specification for Shoulder Prostheses.

It should be understood that the various illustrated arrangements for mounting a domed pyrocarbon shell to a metal substructure is not limited to humeral head implants, but similar designs can be used to attach pyrocarbon shells to metal substructures for substantially any orthopedic joint replacement, for example a hip joint replacement. Thus, although the invention has been illustrated with regard to certain preferred embodiments, it should be understood that changes and modifications that would be obvious to one having the ordinary skill in this art may be made without deviating from the scope of this invention which is defined by the claims appended hereto. For example, although the illustration is generally one in which the metal substructure includes a female cavity for operation as part of a taper lock connection to a stem, the reverse construction, as shown in FIG. 17, might alternatively be employed. Likewise, other suitable connections between the metal substructure and a stem can be used; for example, the interior screw threads shown in FIG. 8E might be used so long as a locking arrangement is preferably incorporated. Although dimensioning the groove in the intermediate element to be wider than that in the metal substructure is preferred, the reverse would also be feasible for some of the embodiments shown. Moreover, instead of employing a split ring or other such collapsible-expandable ring, other retaining mechanisms may be used, as by including teeth or detents on the metal substructure that would engage cavities in an intermediate element, or by providing interengaging elements on the metal substructure and the intermediate element as depicted in FIGS. 20 and 22.

Particular features of the invention are emphasized in the claims that follow.

The invention claimed is:

1. An implant for providing a replacement articulating surface for a head of one bone member of an orthopedic joint, which implant comprises:
   a pyrocarbon shell having an outer convex surface which is a section of a sphere that will serve as an articulating surface, a concave domed interior surface and an open proximal base that is formed to terminate at an inward-extending rim,
   a metal substructure having a convex distal surface and means at a proximal end thereof for securing the implant in a cavity formed at an end of the bone member,
   an intermediate element of flexible polymeric material which has a radially outer surface near a base thereof, which radially outer surface is of greater diameter than an interior diameter of said inward-extending rim, and which is sufficiently flexible to allow insertion of said intermediate element axially into said open proximal base of said pyrocarbon shell to create a fit where there is nonadhesive physical interference between said intermediate element radially outer surface and said inward-extending rim at the base of said pyrocarbon shell that prevents withdrawal of said intermediate element from said pyrocarbon shell, creating a subassembly of said shell and said intermediate element,
   said intermediate element having a cylindrical interior surface section and said metal substructure having a cylindrical surface section, and said metal substructure and said intermediate element being mated with each other so that said cylindrical surfaces juxtapose, and
   interengaging means at a specific location along said juxtaposed cylindrical surfaces which allows said metal substructure to be inserted fully into said subassembly but physically prevents subsequent disassembly by withdrawal of said metal substructure therefrom, whereby forces at said joint are transferred compressively through said pyrocarbon shell to said convex distal surface of said metal substructure when the implant is in place at said joint.

2. The implant according to claim 1 wherein said mating sections are right circular cylindrical surfaces and said proportioning is such as to create a press fit therebetween.

3. The implant according to claim 1 wherein said intermediate element is an annular element having a groove in its cylindrical interior surface section and having an outward facing annular arcuate surface at a distal end thereof, which annular surface juxtaposes with said concave domed interior surface of said pyrocarbon shell.

4. The implant according to claim 3 wherein said metal substructure cylindrical surface section is a right circular cylindrical surface which is proportioned to form a press fit with said cylindrical interior surface section of said intermediate element which is also a right circular cylindrical surface and wherein said metal substructure is proportioned so that said convex distal surface thereof substantially abuts said concave domed interior surface of said pyrocarbon shell in the implant when assembled.

5. The implant according to claim 3 wherein said metal substructure is proportioned so that, when assembled with said subassembly of said pyrocarbon shell and said annular intermediate element and when said interengaging means is engaged, there is space between said convex distal surface of said metal substructure and said concave domed interior surface of said pyrocarbon shell, wherein said space is filled with a solidified material that was fluid when it was deposited in a cavity provided by the concave domed interior surface of said pyrocarbon shell, so that said solidified material now transmits forces between said pyrocarbon shell in compression and said metal substructure.

6. An implant for providing a replacement articulating surface for a head of one bone member of an orthopedic joint, which implant comprises:
   a pyrocarbon shell having an outer convex surface which is a section of a sphere that will serve as an articulating surface, a concave domed interior surface and an open proximal base, a metal substructure having a convex distal surface and means at a proximal end thereof for securing the implant in a cavity formed at an end of the bone member, and an intermediate element of polymeric material which is sufficiently flexible to allow insertion of said intermediate element axially into said open proximal base of said pyrocarbon shell and to create a fit where there is physical interference that prevents withdrawal of said intermediate element from said pyrocarbon shell, creating a subassembly of said shell and said intermediate element, said intermediate element having a cylindrical interior surface section and said metal substructure having a cylindrical surface section proportioned to juxtapose with said cylindrical interior surface section of said intermediate element, and said intermediate element and said metal substructure having interengaging means which allows said metal substructure to be inserted fully into said subassembly but prevents withdrawal of said metal substructure therefrom, said interengaging means comprising grooves in said cylindrical surface sections that face each other and align with each other when said metal substructure is fully inserted into said subassembly, and an expandable retainer that is completely received in the groove in said metal substructure that expands and resides partially in each of said grooves after insertion of said metal substructure into said subassembly, an axial width of either of said grooves being such that load applied to said articulating surface of said pyrocarbon shell cannot be transferred between said metal substructure and said shell via said retainer and thus is transferred to said convex distal surface of said metal substructure through compression of said pyrocarbon shell.

7. The implant according to claim 6 wherein said expandable retainer is a flat metal split ring which can be collapsed to fit entirely within said groove in said metal substructure.

8. The implant according to claim 6 wherein said intermediate element has a convex domed outer surface section which substantially abuts said concave domed interior surface of said pyrocarbon shell.

9. The implant according to claim 8 wherein said convex domed outer surface section of said intermediate element is a spheroidal surface.

10. The implant according to claim 8 wherein said convex domed outer surface section of said intermediate element is a spherical surface.

11. The implant according to claim 10 wherein said convex distal surface of said metal substructure is spherical and at a base thereof, surmounts said cylindrical surface section which is a right circular cylindrical surface, wherein said intermediate element has a similar interior concave spherical surface and a right circular cylindrical surface which surfaces juxtapose with said metal substructure spherical and right circular cylindrical surfaces when assembled to form the implant, and wherein said groove in said cylindrical interior surface section of said intermediate element is of greater axial width and is located so that, in the implant, the greater width of said groove provides annular space which lies distally of said retainer.

12. The implant according to claim 11 wherein, at regions of transition between said spherical and right circular cylindrical surfaces of said intermediate element and said metal substructure, clearances are provided to create a thin annular space of such a dimension that any potential contact at a region near said regions of transition is avoided that might prevent full contact between said intermediate element interior concave spherical surface and said metal substructure convex distal surface.

13. An implant for providing a replacement articulating surface for a head of one bone member of an orthopedic joint, which implant comprises:

a pyrocarbon shell having an outer convex surface which is a section of a sphere, an interior concave domed surface and an open proximal base, a metal substructure having a convex distal surface, a proximal cylindrical surface section and means at a proximal end thereof for securing the implant in a cavity formed at an end of the bone member, and an intermediate element of flexible polymeric material which has a convex domed outer surface distal section, that substantially abuts said interior concave domed surface of said pyrocarbon shell, and has a proximal cylindrical interior surface section, and which is sufficiently flexible to allow axial insertion of said intermediate element into said open proximal base of said pyrocarbon shell and to create a subassembly of said pyrocarbon shell and said intermediate element, where there is physical interference between said pyrocarbon shell and said intermediate element that prevents withdrawal of said intermediate element from said pyrocarbon shell, said metal substructure being mated with said intermediate element so that said proximal cylindrical surface section juxtaposes with said proximal cylindrical interior surface section of said intermediate element, and said intermediate element and said metal substructure having interengaging elements formed at a specific location along said proximal cylindrical surface section of said metal substructure and said proximal cylindrical interior surface of said intermediate element which interengaging elements comprise an inwardly-protruding bead on said proximal cylindrical interior surface section and a shallow groove in said proximal cylindrical surface section of said metal substructure which shallow groove is aligned with said inwardly-protruding bead, which interengaging elements allow said metal substructure to be inserted fully into said subassembly but prevent subsequent disassembly by withdrawal of said metal substructure therefrom, whereby forces at said joint are transferred compressively through said pyrocarbon shell and said intermediate element to said convex distal surface of said metal substructure when the implant is in place at said joint.

14. The implant according to claim 13 wherein said shallow groove is of rectangular cross-section and of an axial dimension greater than a corresponding dimension of said inwardly-protruding bead.

15. The implant according to claim 13 wherein said shallow groove is of arcuate cross-sectional shape and is positioned so as to, in fully-assembled condition, create physical interference between said shallow groove and said inwardly-protruding bead after deformation of said inwardly-protruding bead upon insertion of said metal substructure that prevents said bead's return to an initial configuration and results in a thrusting of said convex distal surface of said metal substructure into tight engagement with a convex domed interior surface of said intermediate element.

16. An implant for providing a replacement articulating surface for the head of the humerus in the shoulder joint, which implant comprises:

a pyrocarbon shell having an outer convex distal articulating surface which is a section of a sphere, a concave interior surface and an open proximal base, a metal substructure having a convex distal surface and means at a proximal surface thereof for securing the implant in a cavity formed at an end of the humerus, and an intermediate element of flexible polymeric material in the form of a shell which is sufficiently flexible to allow insertion of said intermediate element axially into said open proximal base of said pyrocarbon shell and to create a subassembly of said pyrocarbon shell and said intermediate element where there is physical interference between said pyrocarbon shell and said intermediate element that prevents withdrawal of said intermediate element from said pyrocarbon shell and said intermediate element having a convex outer surface section which substantially abuts said concave interior surface of said pyrocarbon shell, said intermediate element having a cylindrical interior surface section and said metal substructure having a cylindrical surface section proportioned to juxtapose with said cylindrical interior surface section of said intermediate element, said intermediate element and said metal substructure having facing grooves in said cylindrical surface sections that align with each other when said metal substructure is fully inserted into said subassembly, and an expandable retainer that is completely received in said groove in said metal substructure and that expands and resides partially in each of said facing grooves after insertion of said metal substructure into said subassembly, whereby forces at said shoulder joint are transferred compressively through said pyrocarbon shell to said convex distal surface of said metal substructure when the implant is in place at said shoulder joint.

17. The implant according to claim 16 wherein said cylindrical surface sections are right circular cylindrical surfaces and said proportioning is such as to create a press fit therebetween.

18. The implant according to claim 17 wherein said expandable retainer is a flat metal split ring which can be collapsed to fit entirely within said groove in said metal substructure, and wherein said grooves in said intermediate element and said metal substructure have widths measured axially which are such that a load applied to said outer convex distal articulating surface of said pyrocarbon shell cannot be transferred between said metal substructure and said pyrocarbon shell via said retainer but can only be transferred through compression of said pyrocarbon shell.

* * * * *